(12) United States Patent
Mansouri et al.

(10) Patent No.: US 11,471,337 B2
(45) Date of Patent: Oct. 18, 2022

(54) 3D PRINTED NASAL PHARYNGEAL AND ORAL SWABS

(71) Applicant: SprintRay Inc., Los Angeles, CA (US)

(72) Inventors: Amir Mansouri, Los Angeles, CA (US); Hossein Bassir, Los Angeles, CA (US)

(73) Assignee: SprintRay Inc., Los Angeles, CA (US)

( * ) Notice: Subject to any disclaimer, the term of this patent is extended or adjusted under 35 U.S.C. 154(b) by 0 days.

(21) Appl. No.: 17/246,296

(22) Filed: Apr. 30, 2021

(65) Prior Publication Data

US 2021/0338491 A1  Nov. 4, 2021

Related U.S. Application Data

(60) Provisional application No. 63/018,459, filed on Apr. 30, 2020.

(51) Int. Cl.
*A61F 13/38*  (2006.01)
*B33Y 80/00*  (2015.01)
*A61B 10/00*  (2006.01)

(52) U.S. Cl.
CPC ........ *A61F 13/385* (2013.01); *A61B 10/0051* (2013.01); *B33Y 80/00* (2014.12)

(58) Field of Classification Search
CPC ............ A01K 67/033; A01K 2227/706; A23K 10/24; A23K 50/90; B33Y 80/00
See application file for complete search history.

(56) References Cited

U.S. PATENT DOCUMENTS

| | | | |
|---|---|---|---|
| 2009/0291944 A1* | 11/2009 | Ash | A01N 43/84 514/227.5 |
| 2019/0090801 A1* | 3/2019 | Rogers | A61B 5/6868 |
| 2019/0151335 A1* | 5/2019 | Altschul | A61K 9/0019 |
| 2019/0247050 A1* | 8/2019 | Goldsmith | A61B 17/12181 |
| 2020/0146425 A1* | 5/2020 | Crapet | A46B 9/021 |
| 2020/0146429 A1* | 5/2020 | Crapet | A46B 3/005 |
| 2020/0237086 A1* | 7/2020 | Crapet | A46B 1/00 |
| 2021/0137735 A1* | 5/2021 | Minelli | A46B 3/005 |
| 2021/0186183 A1* | 6/2021 | Crapet | A46B 9/005 |
| 2021/0213264 A1* | 7/2021 | Liu | A61M 37/0015 |
| 2021/0394391 A1* | 12/2021 | Minary-Jolandan | B33Y 80/00 |

* cited by examiner

*Primary Examiner* — Rick K Chang
(74) *Attorney, Agent, or Firm* — Jafari Law Group, Inc.

(57) ABSTRACT

The invention is generally a nasal pharyngeal and oral swab that may be mass-produced via three-dimensional (3D) printing. To achieve the right materials for 3D printing the swabs, exemplary embodiments employ a set of materials that result in a rigid structure that has bendable properties (at least in the neck or stem region of the swab), but more rigid and bridle properties at a breakpoint of the swab. In exemplary embodiments, this may be achieved by constructing the device of a first photosensitive material that is generally soft and bendable when cured, and a second photosensitive material that is generally rigid and brittle when cured, wherein the soft bendable material comprises of about 70% to 90% of the photosensitive composition used to 3D print the swab, and the rigid and brittle material comprises of about 30% to 10% of the photosensitive composition used to 3D print the swab.

13 Claims, 12 Drawing Sheets

FIG. 1A
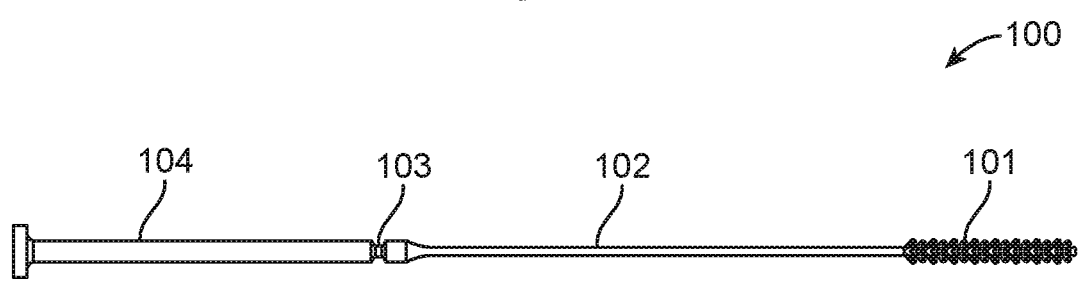
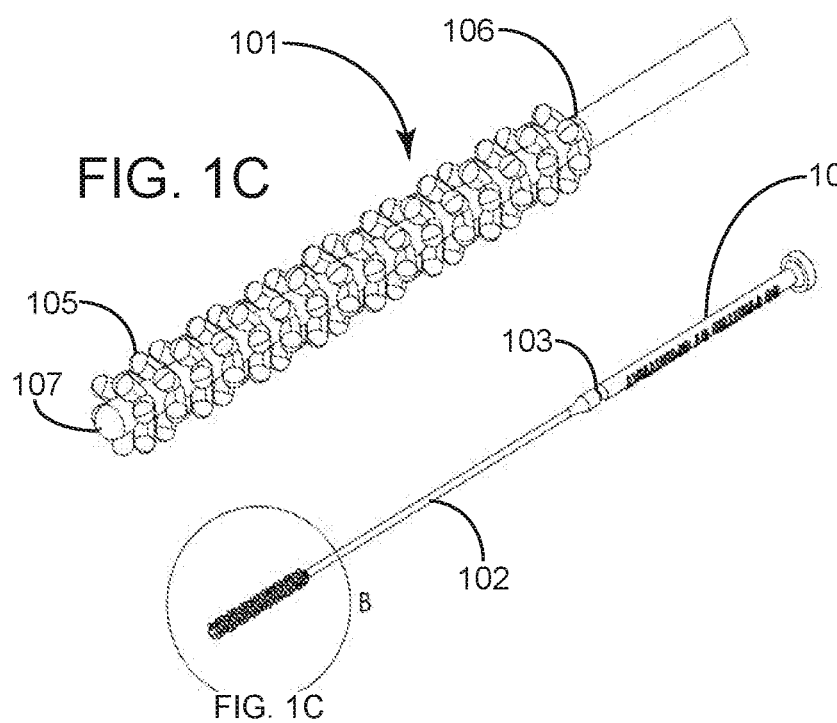
FIG. 1B
FIG. 1C

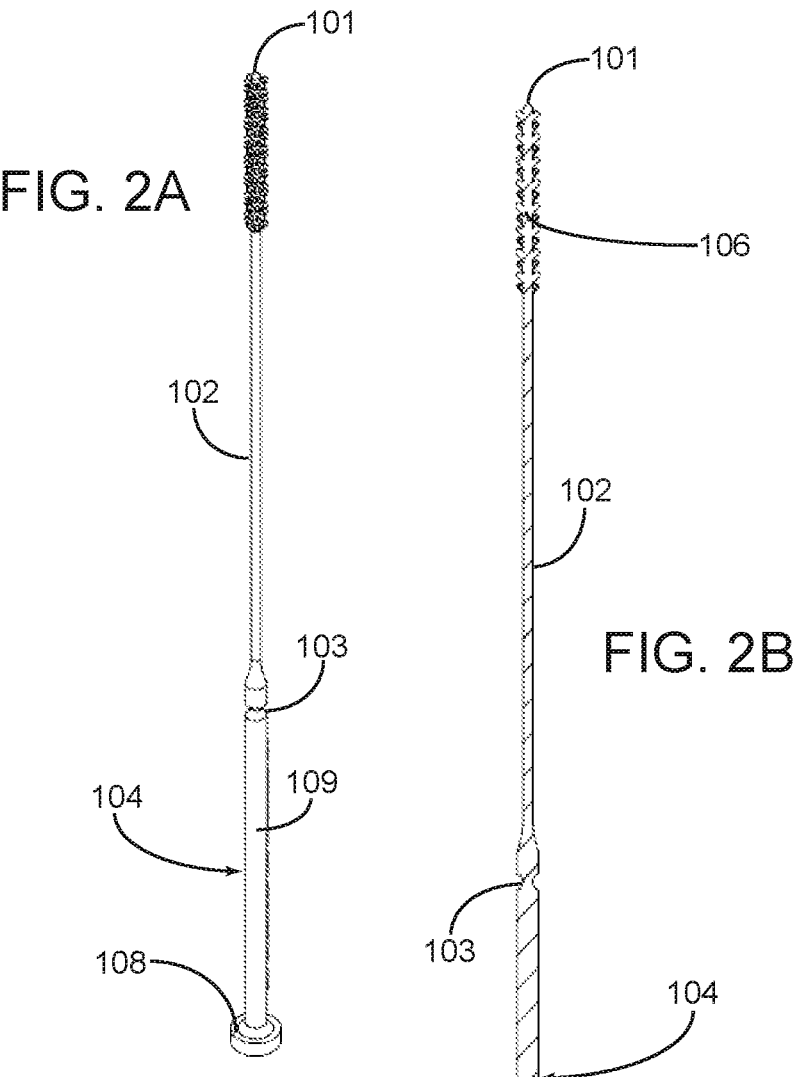

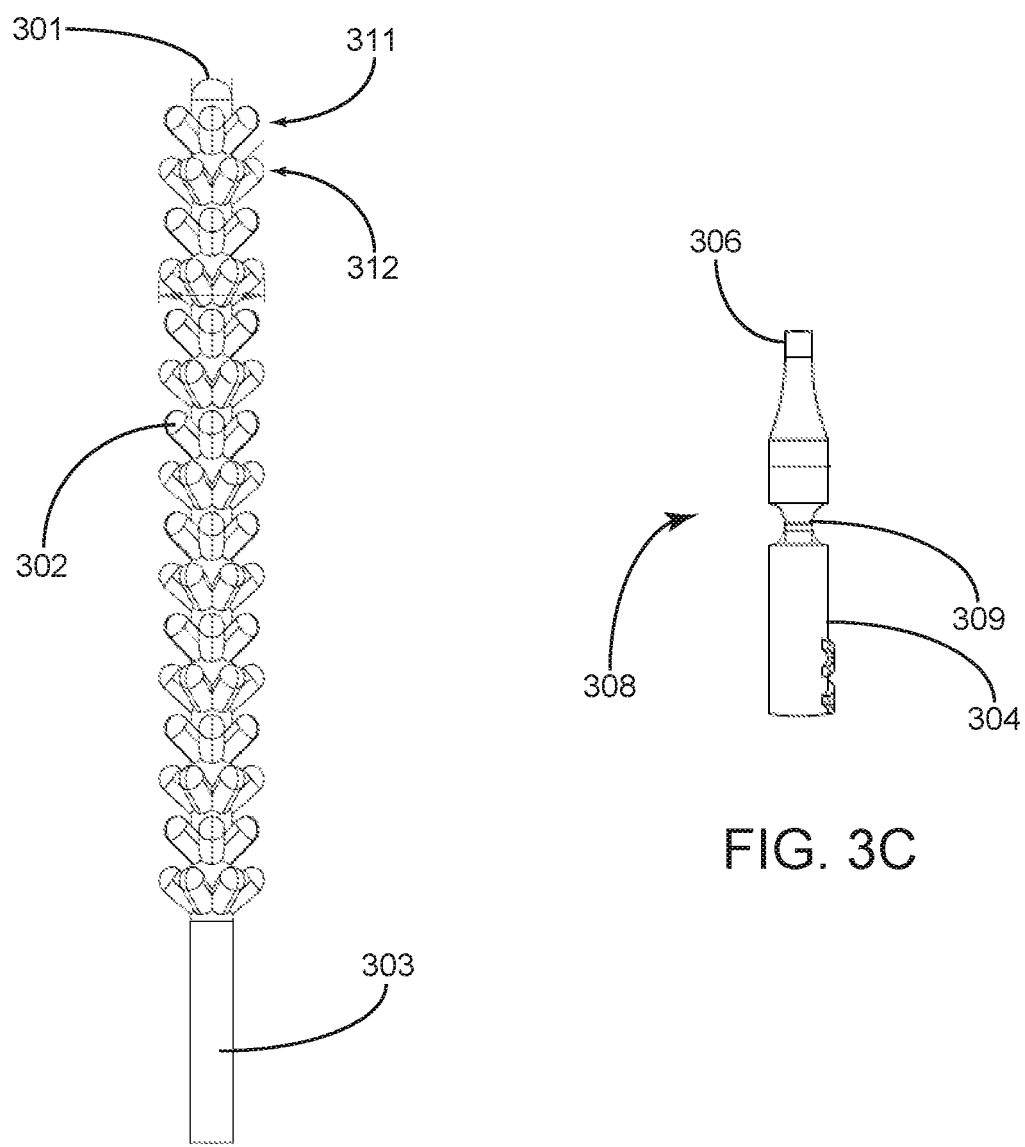

3D PRINTED NASAL PHARYNGEAL AND ORAL SWABS

PRIORITY CLAIM

This is a Non-provisional Application that claims priority to U.S. Provisional Application No. 63/018,459, filed on Apr. 30, 2020, the entire disclosure of which is incorporated by reference in its entirety.

TECHNICAL FIELD OF THE INVENTION

The present invention relates generally to nasal and oral swabs. More specifically, the present invention relates to nasal and oral swabs that may be three-dimensionally (3D) printed.

COPYRIGHT AND TRADEMARK NOTICE

A region of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

At the time of the filing of this application the world is experiencing a pandemic. The current situation involves a virus that has been identified as COVID-19. As Covid-19 cases are rising, there is a tremendous shortage of the nasopharyngeal swabs for testing. Lack of a testing kit has led some hospitals to turn sick patients away. Current tests for the COVID-19 virus, but also for other similar viruses that attack the respiratory system, rely on nasal pharyngeal and oral swabs.

A throat swab or a nasal swab may be used to collect samples from the throat or nasal passage of a subject. A nasal swab may be useful for testing for upper respiratory diseases and a throat swab may be useful for testing lower respiratory disease. Swabs are usually used for testing respiratory infections such as influenza. Nasopharyngeal swabs are flexible sticks that insert into the nose to the back of the nasal cavity and then collect samples on the bristles end of the swab (collection tip). A cultural medium is then used to hold the samples which in this case is the swab bristles end that can easily separate from the rest of the swab.

During an outbreak, for example the ongoing pandemic, a critical problem is the sheer number of tests that are required to be deployed to a population, whether local, regional, or global. One way to tackle the problem of rapidly producing great numbers of swabs is via rapid manufacturing methods such as 3D printing. 3D printing, also known as additive manufacturing (AM), rapid prototyping (RP), or solid freeform fabrication (SFF), is an advanced manufacturing process to additively create 3D objects from computer-aided design (CAD) data directly. The machine which performs the process is called a 3D printer. Compared with traditional manufacturing processes, such as milling, drilling, and injection molding, in which the object is fabricated through removing excess material from a block or changing the shape of the material, 3D printing fabricates 3D objects through selectively depositing material or energy on a single layer, and then accumulating layers one upon another to form 3D objects. Because of its unique means to create 3D objects, parts with complex shapes and intricate geometric features, which are usually not accessible through traditional manufacturing processes, could be fabricated through 3D printing. 3D printing is a collection of different techniques.

SprintRay, Inc. is a 3D Printing Company that is rapidly responding to the COVID-19 crisis. The company can mass produce 3D printed products for hospitals or other facilities or agencies capable of addressing the needs of thousands of patients. Regarding swabs for testing kits, including but not limited to testing kits for COVID-19, several problems persist that have not been adequately addressed, including the mass manufacturing of nasal and oral swabs for providing the same to hospitals and institutions trying to combat the ongoing problem, and that will be required to combat future outbreaks of infectious diseases. It is to these ends that the present invention has been developed.

BRIEF SUMMARY OF THE INVENTION

According to the present invention, a nasal pharyngeal and oral swab that may be three-dimensionally (3D) printed and mass-produced is described.

Generally, the invention is a 3D printed nasopharyngeal and oral swab that is easy to mass produce. To achieve the right materials for 3D printing the swabs, exemplary embodiments employ a set of materials that result in a rigid structure that has bendable properties (at least in the neck or stem region of the swab), but more rigid and bridle properties at a breakpoint of the swab. In exemplary embodiments, this may be achieved by constructing the device of a first photosensitive material that is generally soft and bendable when cured, and a second photosensitive material that is generally rigid and brittle when cured. In some exemplary embodiments, the first or soft bendable material comprises of about 70% to 90% of the photosensitive composition used to 3D print the swab. In some exemplary embodiments, the second rigid and brittle material comprises of about 30% to 10% of the photosensitive composition used to 3D print the swab.

In one example, a nasal and oral swab is provided. The nasal and oral swab may include: a collection tip including a plurality of protrusions extending diagonally and upwardly from a cylindrical stem, wherein the cylindrical stem extends below and at a distal end of the collection tip to form a cylindrical neck having a first circumference; a body including a base and a cylindrical elongated handle portion having a second circumference that is greater than the first circumference; and a breakpoint that facilitates breaking apart the swab for laboratory testing, the breakpoint removably coupling the body to the cylindrical neck.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF DRAWINGS

Elements in the figures have not necessarily been drawn to scale in order to enhance their clarity and improve understanding of these various elements and embodiments of the present invention. Furthermore, elements that are known to be common and well understood to those in the industry are not depicted in order to provide a clear view of the various embodiments of the invention.

FIG. 1A illustrates the basic components of a 3D printed nasopharyngeal and oral swab in accordance with some exemplary embodiments of the present invention.

FIG. 1B is a perspective view of a 3D printed nasopharyngeal and oral swab in accordance with some exemplary embodiments of the present invention.

FIG. 1C is a close-up view of the collection tip of the 3D printed nasopharyngeal and oral swab shown in FIG. 1B.

FIG. 2A illustrates an isometric view of a 3D printed nasopharyngeal and oral swab in accordance with some exemplary embodiments of the present invention.

FIG. 2B illustrates a cross-sectional view of a 3D printed nasopharyngeal and oral swab in accordance with some exemplary embodiments of the present invention.

FIG. 3B is a close-up view of the collection tip of the 3D printed nasopharyngeal and oral swab shown in FIG. 3A.

FIG. 3C is a close-up view of the breakpoint of the 3D printed nasopharyngeal and oral swab shown in FIG. 3A.

DESCRIPTION OF THE INVENTION

Figure 3A:
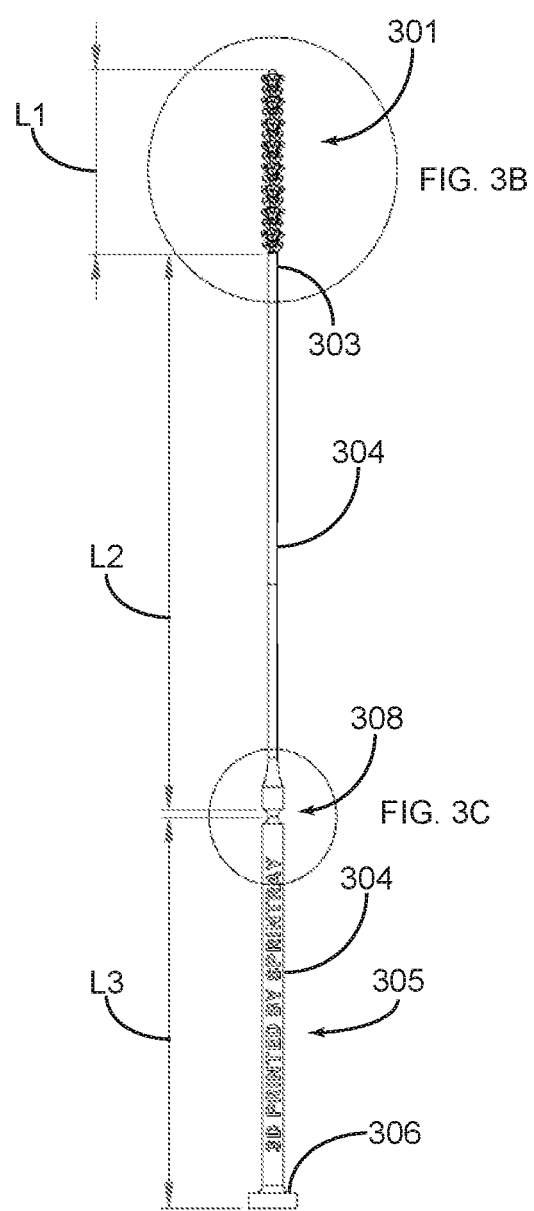
FIG. 3A is a perspective view of a 3D printed nasopharyngeal and oral swab in accordance with some exemplary embodiments of the present invention, depicting exemplary dimensions for a collection tip, neck, breakpoint, and body.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

As used in this disclosure, the term "comprise" and variations of the term, such as "comprising" and "comprises", are not intended to exclude other additives, components, integers or steps. For purpose of description herein, the terms "upper", "lower", "left", "right", "front", "rear", "horizontal", "vertical" and derivatives thereof shall relate to the invention as oriented in figures. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristic relating to the embodiments disclosed herein are not to be considered as limiting, unless the claims expressly state otherwise.

Turning now to the figures, FIG. 1A illustrates the basic components of a 3D printed nasopharyngeal and oral swab in accordance with some exemplary embodiments of the present invention. More specifically, FIG. 1A illustrates an exemplary design of swab 100. In accordance with the present invention. Swab 100 is a 3D printed swab, which as will be further discussed below, can be massed-produced in an array of several swabs that are printed simultaneously in a single batch. Generally, a swab in accordance with the present invention comprises: a collection tip 101, neck 102, breakpoint 103, and body 104.

The collection tip 101 is the portion that functions as a collector for samples from the nasal cavity or mouth of a patient. The neck 102 is the portion that is coupled to a distal end of the collection tip 101 and should be generally bendable to allow swab 100 to be inserted into the patient's nasal cavity, allowing swab 100 to bend along with the cavity. The body 104 is connected to the neck 102 via a breakpoint 103, which will be discussed in turn, and is typically a rigid sold base portion of the swab that functions as a handle and support for the bendable neck, helping guide the collection tip 101 to its intended target within the patient's body.

The breakpoint 103 is a breakable connector between the body 104 and the neck 102 of swab 100. The function of the breakpoint 103 is to break away the neck 102 and collection tip 101 together once the collection efforts have been completed by a health professional or individual taking the sample from the patient. This way, the neck 102 and collection tip 101 portions of the swab 100 may be turned in for laboratory testing and the remaining body 104 may be thrown away.

According to the present invention, the 3D-printed swab 100 has two main benefits: the ability to be manufacture with any shape, and the ability to manufacture multi-material swabs. To these ends, the material or set of materials preferably result in a rigid structure that has bendable properties (at least in the neck region 102 of the swab 100). The material or set of materials must not be too flexible so that the swab is flimsy, for example, because it will be difficult to obtain a sample if the collection tip 101 is not properly supported when being applied during collection. Similarly, the material or set of materials should not result in a very rigid swab; too stiff, and the device will not curve properly along the nasal cavity. Accordingly, swab 100 must be bendable with the right amount of flexibility without deviating from the scope of the present invention.

In development of the present invention, it was discovered that two components are critical to the optimum functionality of a swab 100: the material or set of photosensitive materials and ratios of the photosensitive materials used in the 3D printing process; and the dimensions of the swab or components of the swab constructed using the photosensitive materials.

In exemplary embodiments, this may be achieved by constructing the device of a first photosensitive material that is generally soft and bendable when cured, and a second photosensitive material that is generally rigid and brittle when cured. In some exemplary embodiments, the first or soft bendable material comprises between 70% to 90% of the photosensitive composition used to 3D print the swab. In some exemplary embodiments, the second rigid and brittle material comprises between 30% to 10% of the photosensitive composition used to 3D print the swab.

In exemplary embodiments, the device is constructed of two materials, whereby body 104 of swab 100 comprises a first photosensitive material that is generally soft and bendable when cured, and collection tip 101 of the swab is constructed of a second photosensitive material that is generally rigid and brittle when cured. This may be achieved by printing collection tip 101 of the swab using a first material, and printing body 104 of swab using 100 using the second material.

FIG. 1B is a perspective view of a 3D printed nasopharyngeal and oral swab in accordance with some exemplary embodiments of the present invention. FIG. 1C is a close-up view of the collection tip 101 of the 3D printed nasopharyngeal and oral swab 100 shown in FIG. 1A. The design of the tip defines how efficient the swab collects samples from nasal and oral cavities of patients. For example, and without deviating from the scope of the present invention, one design of a collection tip 101 may include the cattail design shown in FIG. 1C, in which a plurality of elongated protrusions 105 extend diagonally and upwardly from a center stem 106 of the collection tip 101, wherein the top of the collection tip 101 includes a smooth rounded top 107 to prevent injury when placed through the nasal cavity. A similar design is disclosed and discussed with reference to FIG. 3A-FIG. 3C.

In some exemplary embodiments, different shapes may be formed at the collection tip 101 for facilitating sample collection efforts, including for example a honeycomb design which will be discussed with reference to other figures below. Although several collection tip 101 designs are disclosed below, it should be appreciated that a variety of collection tip designs may be implemented in accordance with the present invention, since 3D printing facilitates changing a collection tip design with relative ease.

Turning now to the next set of figures, FIG. 2A illustrates an isometric view of a 3D printed nasopharyngeal and oral swab in accordance with some exemplary embodiments of the present invention; and FIG. 2B illustrates a cross-sectional view thereof. From the cross-sectional view, it can be appreciated that the collection tip 101 comprises a center stem region 106 from which protrusions that are cylindrical in shape extend diagonally and upwardly from said stem 106. The body 104 includes a base portion 108 having a larger circumference than a cylindrical elongated handle portion 109 that facilitates holding and controlling the device when being applied for collection efforts. The neck 102, which is significantly smaller in diameter than the cylindrical handle of the body 104, merges directly to the stem of the collection tip 101. The breakpoint 103 that facilitates breaking apart the swab for laboratory testing, removably connects the body 104 to the neck 102.

Turning now to the next set of figures, FIG. 3A is a perspective view of a 3D printed nasopharyngeal and oral swab in accordance with some exemplary embodiments of the present invention, depicting exemplary dimensions for a collection tip, neck, breakpoint, and body; FIG. 3B is a close-up view of the collection tip of the 3D printed nasopharyngeal and oral swab shown in FIG. 3A; and FIG. 3C is a close-up view of the breakpoint of the 3D printed nasopharyngeal and oral swab shown in FIG. 3A.

In exemplary embodiments, a nasal and oral swab in accordance with the present invention includes: a collection tip 301 including a plurality of protrusions 302 extending diagonally and upwardly from a cylindrical stem 303, wherein the cylindrical stem 303 extends below and at a distal end of the collection tip 301 to form a cylindrical neck 304 having a first circumference; a body 305 including a base 306 and a cylindrical elongated handle portion 307 having a second circumference that is greater than the first circumference; and a breakpoint 308 that facilitates breaking apart the swab for laboratory testing, the breakpoint 308 removably connecting the body 305 to the cylindrical neck 304.

In exemplary embodiments, the breakpoint 308 includes a bridle region 309 comprising a third circumference that is smaller than the first and second circumference for facilitating breaking away the body from the neck of the swab.

As may be appreciated from FIG. 3A, the different regions of the swab may have different lengths. In exemplary embodiments, the ratio of the neck may be between 55%-57% of the total length of the swab. For example, L2 may form about 55%-57% of the total length (L1+L2+L3) so that a length of the neck is slightly longer than a length of the collection tip and handle combined.

From FIG. 3B, it may be appreciated that in some embodiments, by way of example and without limiting the scope of the present invention, the protrusions 302 extend radially from the stem 303 with alternating rows having different number of protrusions so that one row of protrusions includes a first number of protrusions radially extending from the stem 303, and a subsequent adjacent row includes a second number of protrusions extending from stem 303. In some exemplary embodiments, a first row 311 may include 6 protrusions, and a subsequent adjacent row 312 may include 7 protrusions.

Figure 4A:
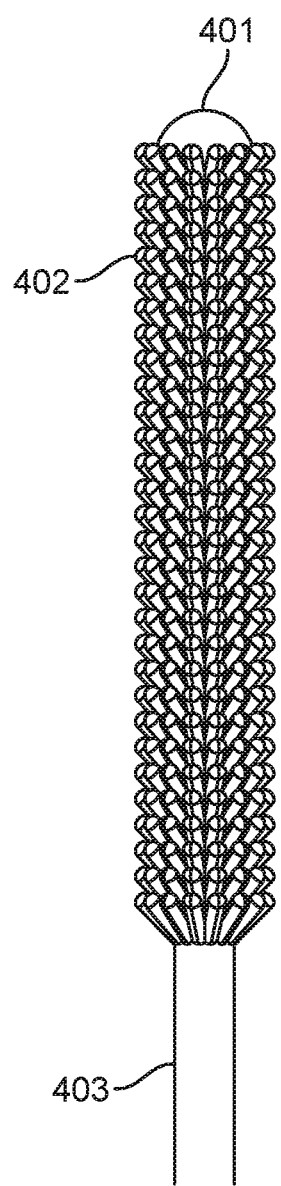
FIG. 4A is a close-up view of one exemplary embodiment of a collection tip for a 3D printed nasopharyngeal and oral swab in accordance with some embodiments of the present invention.
Figure 4B:
FIG. 4B illustrates exemplary dimensions for an exemplary 3D printed nasopharyngeal and oral swab in accordance with some embodiments of the present invention.

Turning now to the next set of figures, FIG. 4A is a close-up view of one exemplary embodiment of a collection tip for a 3D printed nasopharyngeal and oral swab in accordance with some embodiments of the present invention; and FIG. 4B illustrates dimensions in varying units for an exemplary 3D printed nasopharyngeal and oral swab in accordance with some embodiments of the present invention.

In FIG. 4A, another exemplary embodiment of a collection tip is shown. In this exemplary embodiment, a similar cattail design is generated using 3D printing techniques, the design including a head or tip 401 that is smooth and rounded so as to avoid injury to the patient. As with the previously discussed cattail design, this design also includes a plurality of protrusions 402 that radiate from a top portion of a stem 403 of the swab. Each protrusion comprises a cylindrical or substantially cylindrical surface area that is able to capture samples from the patient's nasal pharyngeal and oral cavity. In this embodiment, the protrusions 402 extend radially and uniformly so that each row of protrusions includes the same number of protrusions radially extending from the stem 403. In the shown embodiment, by way of example and without limiting the scope of the present invention, the number of protrusions may be 18 or 16 that are situated in rows around a circumference of the stem 403, with each successive row having the same number of protrusions.

FIG. 4B illustrates exemplary dimensions of an optimized swab design. It should be noted that the shown dimensions are exemplarily shown only, and that other similar rations of dimensions may be employed without deviating from the scope of the present invention. In exemplary embodiments, the dimensions are chosen based on the geometry optimization, so a flexible neck is achieved with a stiff and brittle material. In exemplary embodiments, the ratio of the neck may be between 55%-57% of the total height of the swab. In exemplary embodiments, the thickness range may be between 1 mm to 3 mm with the widest portion being at the handle and the thinnest portion at the breakpoint. The feature is achieved when the neck to total ratio is between 55-85%. Anything less than that may cause the neck to be too brittle and any longer may make the neck undesirably flexible.

Figure 5A:
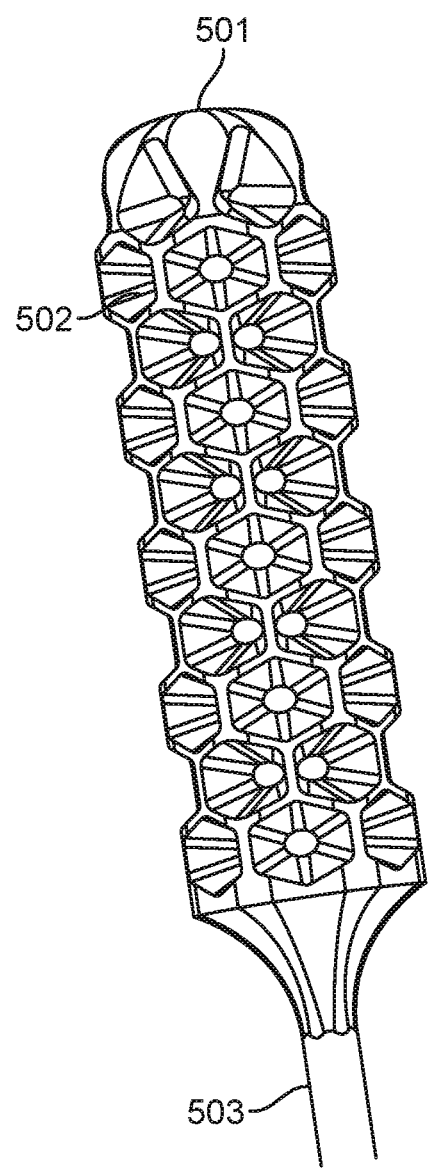
FIG. 5A is a close-up view of one exemplary embodiment of a collection tip for a 3D printed nasopharyngeal and oral swab in accordance with some embodiments of the present invention.
Figure 5B:
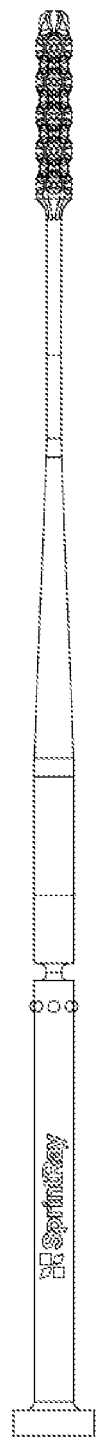
FIG. 5B illustrates exemplary dimensions for an exemplary 3D printed nasopharyngeal and oral swab in accordance with some embodiments of the present invention.

Turning now to the next set of figures, FIG. 5A is a close-up view of one exemplary embodiment of a collection tip for a 3D printed nasopharyngeal and oral swab in accordance with some embodiments of the present invention; and FIG. 5B illustrates dimensions in varying units for an exemplary 3D printed nasopharyngeal and oral swab in accordance with some embodiments of the present invention.

FIG. 5A illustrates another exemplary embodiment of a collection tip, which includes a honeycomb design. In accordance with exemplary embodiments, the honeycomb collection tip may comprise a top region or head 501 that is smooth and rounded so as to avoid injury when the swab is inserted into the patient's nasopharyngeal cavity or mouth. Further, a stem 503 forms a neck portion of the swab. At a topmost region of the stem 503, stem 503 increases in circumference to form a thicker region that is the foundation of the collection tip. This thicker or larger circumference includes a plurality of hexagonal cavities 502 or collector cups that are formed as openings having hexagonal perimeters with triangular inner cavity walls. It will be appreciated that other shapes may be employed without deviating from, or limiting, the scope of the present invention. For example, each cavity could be octagonal, or any other shape. In the present embodiment, the hexagonal cavities 502 form honeycomb shaped surface that facilitate collecting samples from the patient.

FIG. 5B illustrates exemplary dimensions of an optimized swab design. As with the embodiment mentioned above, similar proportions are exemplarily employed in this embodiment. The ratio of the neck may be between 55%-57% of the total height of the swab. The thickness of the neck may be between 1 mm to 3 mm. A ratio of the thickness of the neck to the remainder of the swab may be between 55-85%. Anything less than that may cause the neck to be too brittle and any longer may make the neck undesirably flexible.

Figure 6:
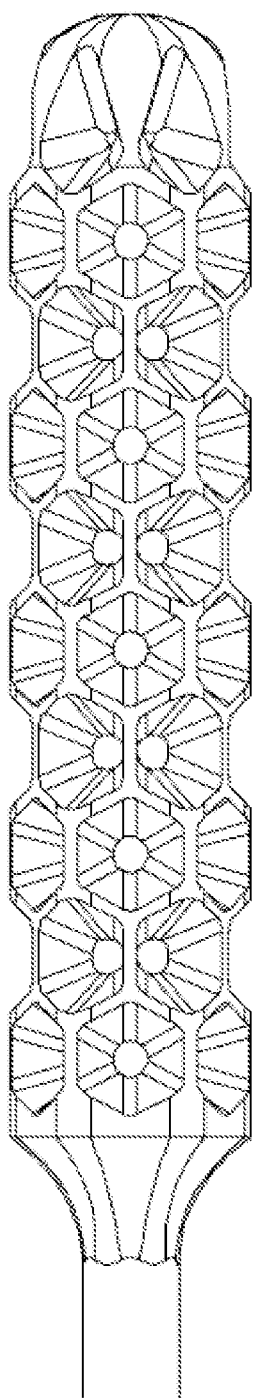
FIG. 6 is another close-up view of a collection tip for a 3D printed nasopharyngeal and oral swab in accordance with some embodiments of the present invention.

FIG. 6 is another close-up view of a collection tip for a 3D printed nasopharyngeal and oral swab in accordance with some embodiments of the present invention.

Figure 7:
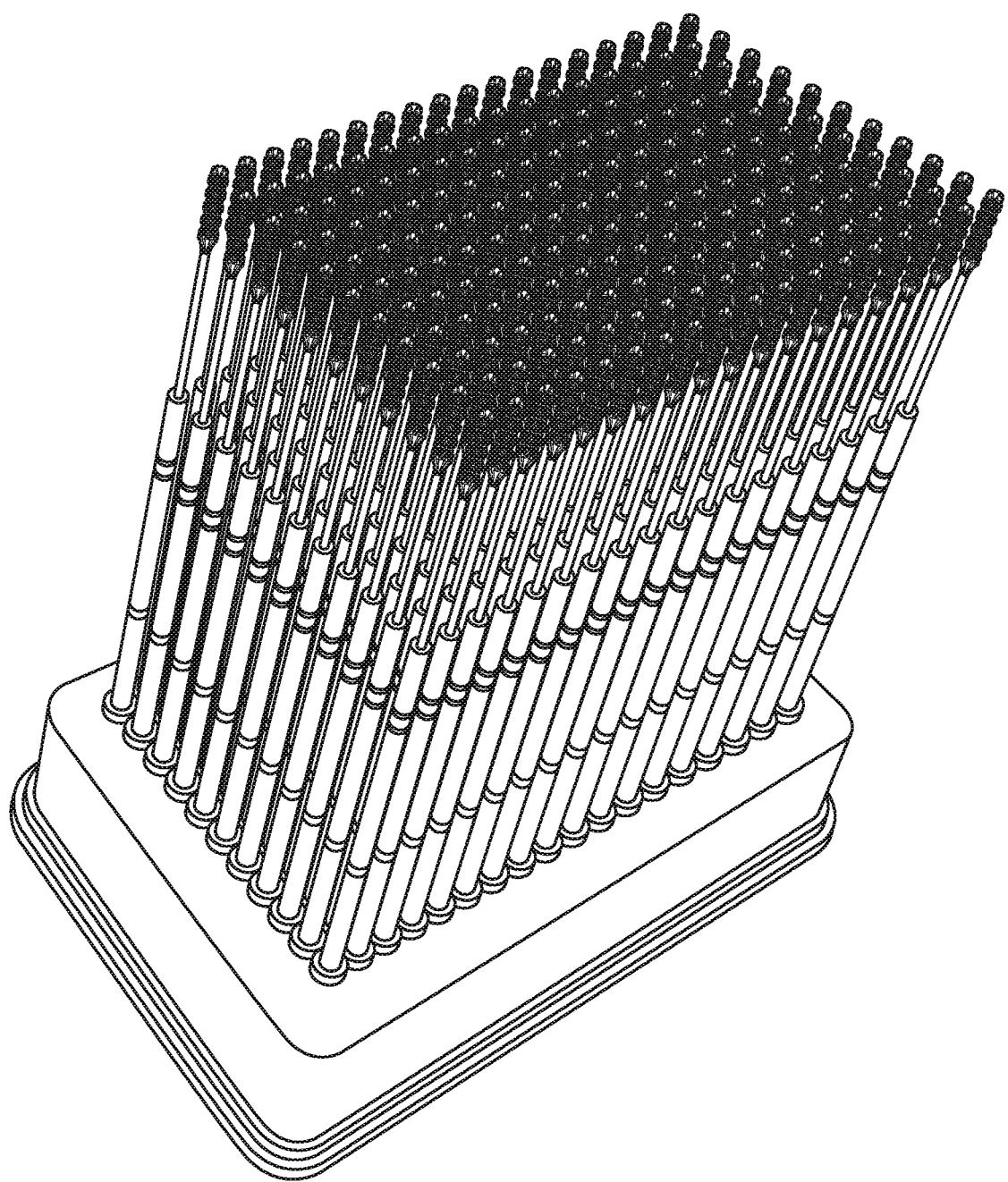
FIG. 7 is an image of an array of multiple 3D printed nasopharyngeal and oral swabs printed at one time, in accordance with the present invention.

FIG. 7 is an image of an array of multiple 3D printed nasopharyngeal and oral swabs printed at one time, in accordance with the present invention. In this manner, a plurality of 3D printers may be deployed during a health crisis in order to address the sheer number of tests that are required to be deployed to a population, whether local, regional, or global.

Figure 8A:
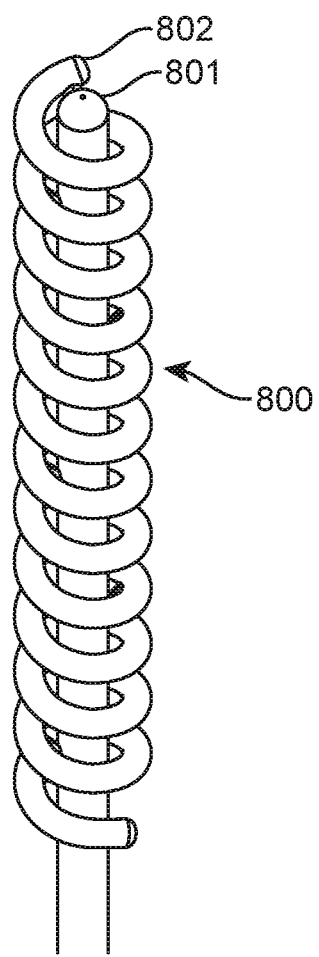
FIG. 8A-FIG. 8C illustrates several close-up views of one exemplary embodiment of a collection tip for a 3D printed nasopharyngeal and oral swab in accordance with some embodiments of the present invention.
Figure 8B:
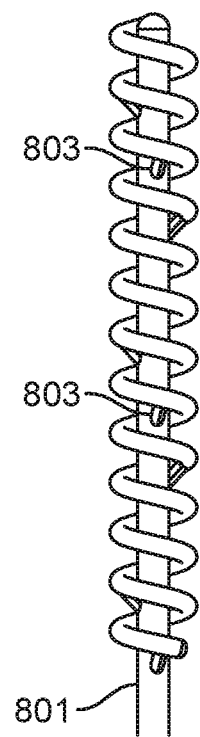
Figure 8C:
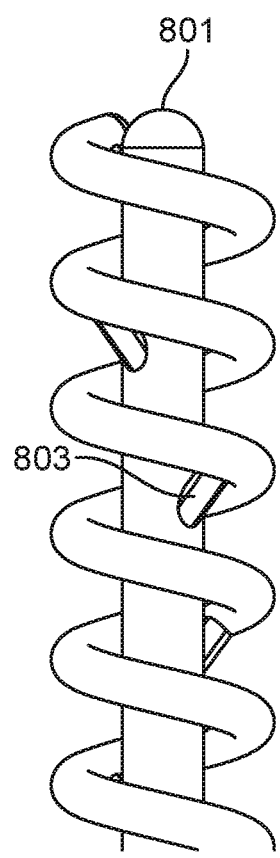

FIG. 8A-FIG. 8C illustrate several close-up views of one exemplary embodiment of a collection tip for a 3D printed nasopharyngeal and oral swab in accordance with some embodiments of the present invention. More specifically, these views depict (clockwise) a perspective view, a side view, and a close-up of the top region of collection tip 800. Generally, collection tip 800 comprises a center support 801 that supports a spiraling support 802, which spirals around central support 801 from a base portion of central support 801 to the top extremity of center support 801. A plurality of supports 803 may extend from central support 801, in some embodiments diagonally from central support 801, in order to secure the spiraling shape of the collection tip 800. One of the advantages of this embodiment is the achieved flexibility of the swab. That is, this construction facilitates flexibility of the collection tip so that it may be sufficiently bendable but sturdy enough so that collection tip 800 is able to retain its shape. In exemplary embodiments, the collection tip is bendable to conform to the nasal cavity, which takes 90 degree turns; this spiral or helical design facilitates such functionality.

Figure 9:
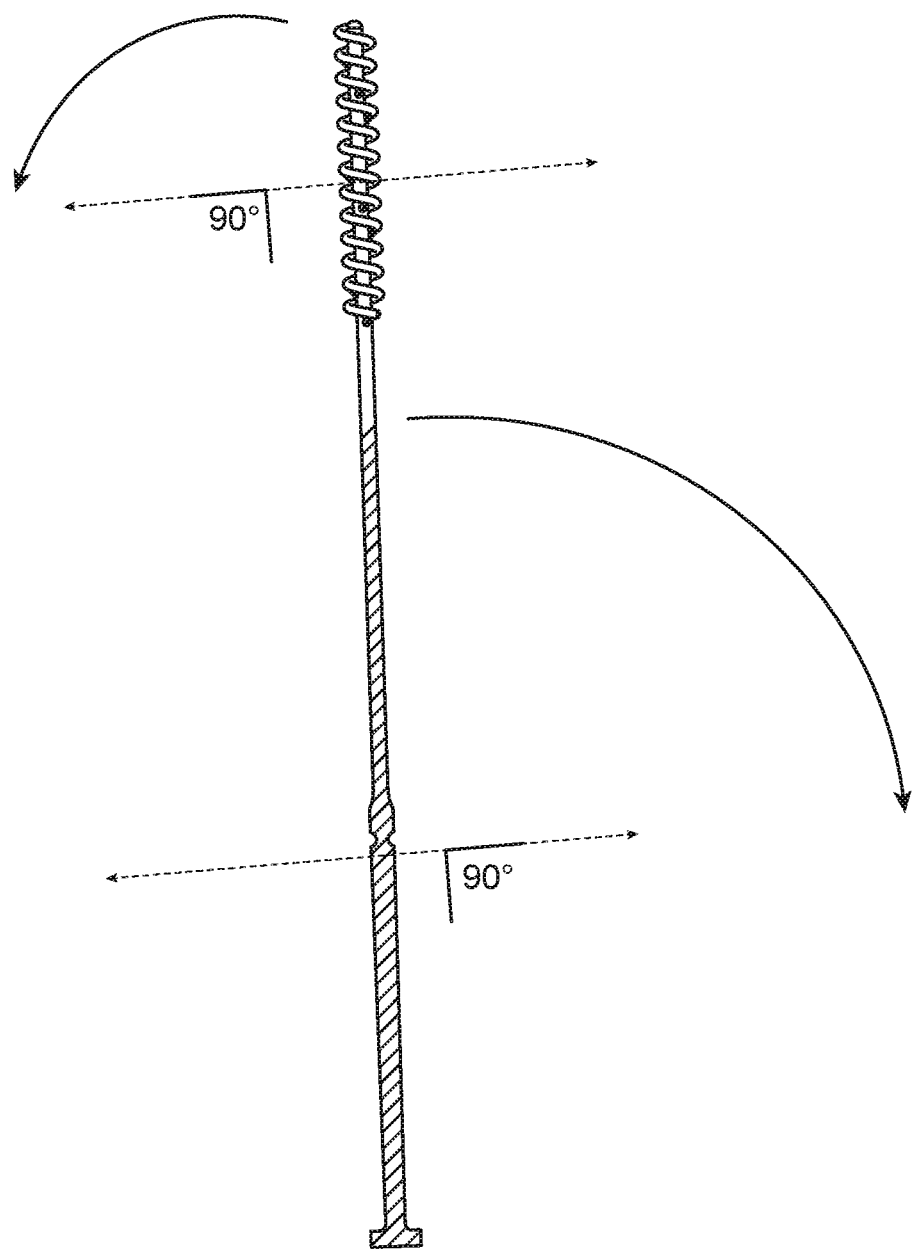
FIG. 9 is a semi-cross-sectional view of one exemplary embodiment of a collection tip for a 3D printed nasopharyngeal and oral swab in accordance with the embodiments shown in FIG. 8.

FIG. 9 is a semi-cross-sectional view of one exemplary embodiment of a 3D printed nasopharyngeal and oral swab in accordance with the embodiments shown in FIG. 8. From this view, it may be appreciated that both the collection tip, as well as the neck of the swab are able to bend at least 90°. In some exemplary embodiments, the neck of the swab is even more so bendable and is capable of bending such that the collection tip can touch the base or body of the swab without breaking or snapping.

A nasal pharyngeal and oral swab has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A three-dimensionally (3D) printed swab, comprising:
a collection tip formed of a first photosensitive material that is rigid and brittle when cured;
a stem extending from a distal end of the collection tip, the stem formed of a second photosensitive material that is soft and bendable when cured; and
a body breakably connected to the stem with a breakpoint between the stem and a handle of the body.

2. The 3D printed swab of claim 1, wherein the first material comprises between 30% to 10% of a photosensitive composition used to 3D print the swab.

3. The 3D printed swab of claim 1, wherein the second material comprises between 70% to 90% of a photosensitive composition used to 3D print the swab.

4. The 3D printed swab of claim 1, wherein the breakpoint includes a bridle region comprising a first circumference that is smaller than a circumference of the handle and a circumference of the stem for facilitating breaking away the body from the stem of the swab.

5. The 3D printed swab of claim 1, wherein a ratio of a neck of the swab may be between 55%-57% of a total length of the swab.

6. The 3D printed swab of claim 1, wherein the collection tip includes a plurality of protrusions that are rounded.

7. The 3D printed swab of claim 1, wherein the collection tip includes a plurality of protrusions that form a honeycomb-shaped surface.

8. The 3D printed swab of claim 1, wherein the collection tip includes a plurality of protrusions extending radially from a center support of the collection tip.

9. The 3D printed swab of claim 8, wherein the plurality of protrusions extend radially in adjacent rows.

10. The 3D printed swab of claim 8, wherein the stem to total length ratio is between 55-85%.

11. The 3D printed swab of claim 1, wherein the collection tip includes a center support that supports a spiraling support that spirals around the center support from a base portion of the central support to a top extremity of the center support.

12. The 3D printed swab of claim 1, wherein the stem of the swab is adapted to bend such that the stem of the swab is able to bend at least 90°.

13. The 3D printed swab of claim 1, wherein the collection tip of the swab is adapted to bend such that the collection tip of the swab is able to bend at least 90°.

* * * * *